(12) United States Patent
Ausich et al.

(10) Patent No.: US 8,377,877 B2
(45) Date of Patent: Feb. 19, 2013

(54) COMPOSITION AND METHOD FOR REDUCING POST-PRANDIAL BLOOD GLUCOSE

(75) Inventors: Rodney Ausich, Des Moines, IA (US); Jerry Newman, West Des Moines, IA (US); Zoriada DeFeitas, Polk City, IA (US); Andrew Shao, West Des Moines, IA (US); Fayad Z. Sheabar, West Des Moines, IA (US)

(73) Assignee: Kemin Foods, L.C., Des Moines, IA (US)

( * ) Notice: Subject to any disclaimer, the term of this patent is extended or adjusted under 35 U.S.C. 154(b) by 0 days.

(21) Appl. No.: 10/426,678

(22) Filed: Apr. 30, 2003

(65) Prior Publication Data

US 2004/0219236 A1 Nov. 4, 2004

Related U.S. Application Data

(63) Continuation-in-part of application No. 09/900,555, filed on Jul. 6, 2001, now Pat. No. 6,767,566.

(51) Int. Cl.
*A61K 38/00* (2006.01)
*A61K 36/81* (2006.01)
*A61K 36/00* (2006.01)

(52) U.S. Cl. ........... 514/6.8; 514/6.9; 514/4.9; 424/723; 424/725

(58) Field of Classification Search ............... 424/195.1, 424/725, 723; 514/6.8, 6.9, 4.9
See application file for complete search history.

(56) References Cited

U.S. PATENT DOCUMENTS

| | | | |
|---|---|---|---|
| 4,793,996 A | 12/1988 | Kennedy | |
| 4,833,128 A * | 5/1989 | Solomon et al. | 514/23 |
| 5,468,727 A * | 11/1995 | Phillips et al. | 514/12 |
| 5,545,672 A | 8/1996 | Knutson | |
| 5,980,870 A * | 11/1999 | Baik et al. | 424/58 |
| 6,414,124 B1 * | 7/2002 | Ryan et al. | 530/412 |
| 6,686,456 B2 * | 2/2004 | Ausich et al. | 530/422 |
| 2002/0183491 A1 * | 12/2002 | Ryan et al. | 530/379 |
| 2003/0092150 A1 * | 5/2003 | Sheabar et al. | 435/184 |
| 2003/0092151 A1 * | 5/2003 | Ausich et al. | 435/184 |
| 2003/0153509 A1 | 8/2003 | Bachovchin | |

FOREIGN PATENT DOCUMENTS

WO  WO 03/003836 A1 * 1/2002

OTHER PUBLICATIONS

Hill et al.; Physiology and Behavior (1990); vol. 48, pp. 241-246.*
WikiAnswers: How Long Does Take to Empty The Small Intestine?; Online URL<http://wiki.answers.com/Q/How_long_does_take_to_empty_the_small_intestine>, pp. 1-5.*
Liddle, R.A., "Regulation of chelecystokinin secretion by intraluminal releasing factors", Am J Physiol, 269: G319-27, 1995.

(Continued)

*Primary Examiner* — Patricia Leith
(74) *Attorney, Agent, or Firm* — Davis, Brown, Koehn, Shors & Roberts, P.C.; Kent A. Herink

(57) ABSTRACT

A nutritional intervention composition for reducing post-prandial blood glucose levels in humans, including between about 0.1 mg and about 500 mg of a proteinase inhibitor that is administered prior to the meal. The composition is effective for treating or ameliorating the effects of hyperglycemia and Type II diabetes. The composition also is effective in combating obesity. The proteinase inhibitor is preferably isolated from plant material, such as potatoes, soy, and beans. Potato proteinase inhibitor II and soybean Bowman-Birk inhibitor are included in the group of effective proteinase inhibitors.

5 Claims, 5 Drawing Sheets

OTHER PUBLICATIONS

Beglinger, C., "Effect of cholecystokinin on gastric motility in humans", Ann NY Acad. Sci., 713: 219-225, 1994.

Beglinger, C., "Overview: Chelecystokinin and eating", Curr Opin Investi. Drugs, 3(4): 587-588, 2002.

Melville, J.C., Ryan, C.A., "Chymotrypsin inhibitor I from potatioes. Large scale preparation and characterization of its subunit components", J Biol. Chem., 247(11): 3445-53, 1972.

Bryant, J. Green, T.R., Gurusaddaiah, T., Ryan, C.A., "Proteinase inhibitor II from potatoes: isolation and characterization of its protomer components", Biochemistry, 15(16): 3418-24, 1976.

Peiken, S.R., Springer, C.J., Dockray, G., Blundell J., Hill, J.E., Calam, J., Ryan, C.A., "Oral administration of proteinase inhibitor II from, potatoes stimulates release of cholecystokinin in man", Gastroenterology, 92: A1570, May 1989.

Hill, A.J., Peikin, S.R., Ryan, C.A., Blundell, J.E., "Oral administration of proteinase inhibitor II from potatoes reduces energy intake in man", Physoil. Behav., 48(2): 241-6, 1990.

Schwartz, J.G., Guan, D., Green, G.M., Phillips, W.T., "Treatment with an oral proteinase inhibitor slows gastric emptying and acutely reduces glucose and insulin levels after a liquid meal in type II diabetic patients", Diabetes Care, 17(4): 255-62, 1994.

Reseland, J.E., Holm, H., Jacobsen, M.B., Jennssen, T.G., Hanssen, L.E., "Proteinase inhibitors induce selective stimulation of human trypsin and chymotrypsin secretion", J.Nutr., Mar. 1996; 126(3) 634-42.

Spiegel, T.A., Hubert, C., Peiken, S.R., Effect of a premeal beverage containing a protease inhibitor from potatoes on satiety in dieting overwieght women (abstract). Presented at the North American Association for the Study of Obesity (NAASO) Annual Meeting 1999.

Vasselli, J.R., Greenfield, D., Schwartz, L., Heymsfield, S.B., Consumption of a pre-meal drink containing protease inhibitor from potatoes decreases hunger and increasees fullness in overweight subjects following a meal(Abstract). Presented at the North American Association for the Study of obesity (NAASO) annual meeting 1999.

Liddle, R.A., "Regulation of CCK secretion in humans", J. Gastroenterol, 35: 181-187, 2000.

Phillips, W.T., Schwartz, J.G, "Decelerating gastric emptying: therapeutic possiblities in type 2 diabetes", Diabet Med, 13(9): S44-8, 1996.

* cited by examiner

COMPOSITION AND METHOD FOR REDUCING POST-PRANDIAL BLOOD GLUCOSE

This application is a continuation-in-part of application Ser. No. 09/900,555, filed Jul. 6, 2001 (patented), now U.S. Pat. No. 6,767,566.

BACKGROUND OF THE INVENTION

The invention relates to compositions for reducing post-prandial blood glucose in humans and, more specifically, to a proteinase inhibitor that delays gastric emptying and reduces post-prandial glycemia which may be beneficial in combating obesity and Type II diabetes.

Regulation of body weight depends on genetic as well as physiologic and lifestyle factors that are known to influence energy balance, such as diet, appetite control, metabolism, and physical activity (Aronne, L. J. (2001) *J Clin Psychiatry* 62, 13-22; Fernandez-Lopez, J. A., Remesar, X., Foz, M. & Alemany, M. (2002) *Drugs* 62, 915-44). Despite measures to combat obesity and an increased awareness of the associated co-morbidities, the condition has become an epidemic, with nearly 60% of Americans classified as overweight or obese (Visscher, T. L. & Seidell, J. C. (2001) *Annu Rev Public Health* 22, 355-75). Since the gene pool has not changed, researchers believe the culprit is primarily due to a combination of environmental and lifestyle influences. A focus on dietary fat as a leading cause of obesity the last several decades has been successful in reducing overall fat intake by Americans (from 40% to just over 30% of total calories, from the 1960's to present), but has done little to stave the rise in obesity rates (Lichtenstein, A. H., Kennedy, E., Barrier, P., Danford, D., Ernst, N. D., Grundy, S. M., Leveille, G. A., Van Horn, L., Williams, C. L. & Booth, S. L. (1998) *Nutr Rev* 56, S3-19; discussion S19-28).

Corresponding with this profound rise in obesity incidence, a similar rise in the consumption of foods higher in processed and refined carbohydrates has been observed (Grundy, S. M. (1998) *Am J Clin Nutr* 67, 563S-72S), along with an increased incidence of type II diabetes (Disdier-Flores, O. M., Rodriguez-Lugo, L. A., Perez-Perdomo, R. & Perez-Cardona, C. M. (2001) *P R Health Sci J* 20, 123-30; Felber, J. P. & Golay, A. (2002) *Int J Obes Relat Metab Disord* 26 Suppl 2, S39-45). These events have led researchers to question the effect of dietary fat on body fat accumulation, and suggest that dietary factors other than fat consumption play an important role in body weight regulation (Willett, W. C. (1998) *Am J Clin Nutr* 67, 556S-562S; Willett, W. C. (2002) *Obes Rev* 3, 59-68). Evidence now exists suggesting that chronic glycemia can lead to increased fat synthesis and storage, and may contribute significantly to the development of obesity and other chronic diseases such as diabetes and cardiovascular disease (Jenkins, D. J., Kendall, C. W., Augustin, L. S., Franceschi, S., Hamidi, M., Marchie, A., Jenkins, A. L. & Axelsen, M. (2002) *Am J Clin Nutr* 76, 266S-73S; Ludwig, D. S. (2002) *JAMA* 287, 2414-23; Leeds, A. R. (2002) *Am J Clin Nutr* 76, 286S-9S). Concerns over safety and efficacy of many anti-obesity products have limited their usefulness. Therefore, developments of natural, safe, and effective nutraceutical and/or medications that can help treat or prevent obesity are essential to mitigate this public health crisis.

Both soybeans and potatoes are sources of proteinase inhibitors (PI's), proteins that have been hypothesized to enhance the release of cholecystokinin (CCK), one of several gut peptides that regulate gastric emptying and satiety in humans (Liddle, R. A. (1995) *Am J Physiol* 269, G319-27; Beglinger, C. (1994) *Ann N YAcad Sci* 713, 219-25; Beglinger, C. (2002) *Curr Opin Investig Drugs* 3, 587-8). Delayed gastric emptying, in turn, has been shown to result in a decreased rate of glucose absorption, and lower post-prandial glucose levels (Lefebvre, P. J. & Scheen, A. J. (1999) *Eur J Clin Invest* 29 Suppl 2, 1-6). Proteinase inhibitor II (PI2) is a naturally occurring 21 kDa dimer and potent trypsin and chymotrypsin inhibitor present in white potatoes (Melville, J. C. & Ryan, C. A. (1972) *J Biol Chem* 247, 3445-53; Bryant, J., Green, T. R., Gurusaddaiah, T. & Ryan, C. A. (1976) *Biochemistry* 15, 3418-24). Previous studies using large doses of highly pure PI2 demonstrated increased CCK release and satiety in humans (Peikin, S. R., Springer, C. J., Dockray, G. J., Blundell, J. E., Hill, A. J., Calam, J. & Ryan, C. A. (1987) *Gastroenterology* 92, A1570; Hill, A. J., Peikin, S. R., Ryan, C. A. & Blundell, J. E. (1990) *Physiol Behav* 48, 241-6; Schwartz, J. G., Guan, D., Green, G. M. & Phillips, W. T. (1994) *Diabetes Care* 17, 255-62). In addition, oral administration of PI2 at high doses in a liquid form has been shown to reduce both post-prandial glucose and insulin levels in humans (Schwartz, et al., supra), supporting the use of PI2 as both a promising hunger management tool and an effective agent to reduce post-prandial glycemia experienced by the body.

The development of an efficient proprietary commercial process providing an extract from potatoes containing PI2 has increased the availability of this compound. It was hypothesized that administration of PI2 extract as a nutraccutical ingredient in a low dose, encapsulated form, prior to a meal, might reduce post-prandial glucose levels. This could have important implications for the use of PI2 as part of a diet to help maintain healthy blood sugar levels and reduce the propensity for weight gain.

SUMMARY OF THE INVENTION

The invention consists of a method for reducing post-prandial glycogen levels in the blood of humans by the oral administration of a proteinase inhibitor or a combination of proteinase inhibitors. The proteinase inhibitor or combination is administered prior to the ingestion of a meal and reduces not only the initial rise in blood glucose following a meal (Δ Glucose or ΔG) but also the integrated area under the blood glucose curve (AUC) following a meal. The proteinase inhibitor(s) is effective for helping to maintain healthy blood sugar levels and for treating persons, such as those with Type II diabetes, which have adverse health effects due to hyperglycemia. Further, the proteinase inhibitor(s) is expected to reduce the propensity for weight gain by reducing the glycemia experienced by the body.

Proteinase inhibitors which exhibit the property include potato proteinase inhibitor II and soybean Bowman-Birk inhibitor, although other proteinase inhibitors with similar amino acid sequences and with similar proteinase inhibition properties may be used. While single proteinase inhibitors have been shown to be effective, combinations of two or more distinct proteinase inhibitors may also be used.

In a preferred embodiment, a proteinase inhibitor product isolated from potatoes is administered orally prior to a meal. The potato proteinase inhibitor extract contains between about 15% and about 25% by weight PI2 and also contains other proteins, including a protein similar but not identical to soybean Bowman-Birk inhibitor. The potato proteinase inhibitor extract is present in an amount between about 1 mg and about 1000 mg per dose, and preferably between about 5 mg and about 100 mg per dose, and most preferably between about 7.5 mg and about 30 mg per dose. The potato proteinase inhibitor is effective to reduce the blood glucose spike following a meal by between about 5% and about 30% and the AUC glucose by between about 5% and about 40%. Another preferred proteinase inhibitor is Bowman-Birk inhibitor, which is typically isolated from soybeans. The Bowman-Birk inhibitor is present in an amount between about 0.1 mg and about 5.0 mg per dose, and preferably between about 0.5 mg and about 2.0 mg per dose. The Bowman-Birk inhibitor is effective to reduce the blood glucose spike following a meal by between about 10% and about 25% and the AUC glucose by between about 5% and about 30%.

It is an object of the present invention to reduce post-prandial glycemia in humans by the oral administration of one or more proteinase inhibitors prior to a meal.

It is a further object of the invention to reduce the initial blood glucose spike following a meal by the oral administration of one or more proteinase inhibitors prior to the meal.

It is another object of the invention to reduce the total area under the curve blood glucose following a meal by the oral administration of one or more proteinase inhibitors prior to the meal.

It is yet a further object of the invention to treat hyperglycemia by the oral administration of one or more proteinase inhibitors.

It is yet another object of the invention to prevent obesity by the oral administration of one or more proteinase inhibitors.

Yet a further object of the invention is to combat Type II diabetes through the administration of one or more proteinase inhibitors either alone or in combination with other medications that are used in combating diabetes.

These and other objects of the invention will be understood by those skilled in the art upon a review of this specification, the associated figures and the appended claims.

DETAILED DESCRIPTION OF PREFERRED EMBODIMENTS

Figure 1A:
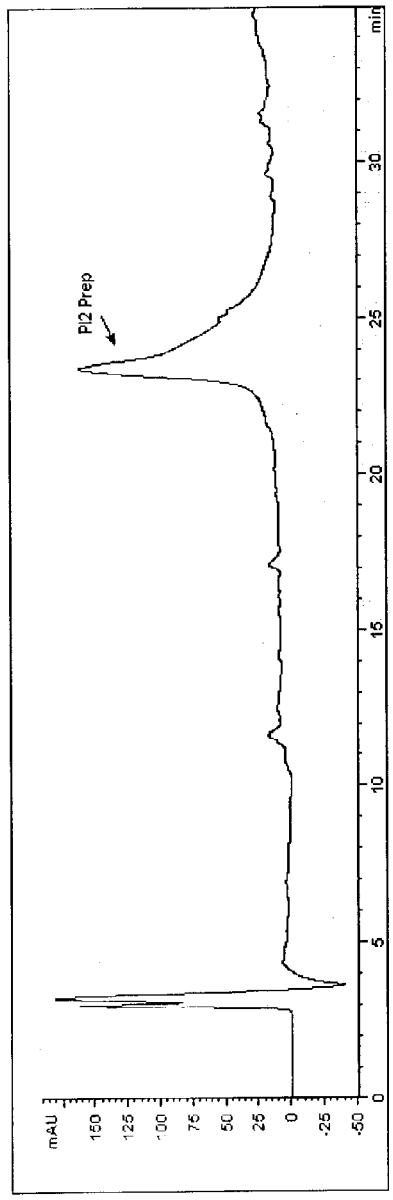
FIGS. 1a and 1b are HPLC chromatograms of the potato PI2 extract used in the experiments and an authentic PI2 standard, respectively.

The composition for reducing post-prandial blood glucose levels in humans is based on a proteinase inhibitor that delays gastric emptying and reduces post-prandial glycemia which may be beneficial in combating obesity and in the therapeutic treatment of patients suffering from hyperglycemia. The proteinase inhibitor is believed to enhance the release of cholecystokinin (CCK), a peptide which regulates gastric emptying. The preferred proteinase inhibitors include potato proteinase inhibitor II and Bowman-Birk inhibitor. In particular, a proteinase inhibitor extracted from potatoes and available commercially from Kemin Consumer Care, L.C., Des Moines, Iowa, under the trademark Bioffect™ was used in some of the examples. Bioffect™ is also available in tablets formulated to contain 15 mg per dose and sold under the trademark Satise™.

The invention is based on the surprising result that proteinase inhibitors administered orally before a meal have the effect of reducing the initial post-prandial glucose spike and also reduce the total integrated area under the curve blood glucose over more than three hours after a meal. Also surprising is that the proteinase inhibitors are effective when administered in a dose in the less than ten milligram range.

EXAMPLE 1

Methods
Subjects

Twenty-six men and 13 women, mean age 35 years (range 23-61 years) with a mean body mass index of 27 (range 23-32) participated in the study. Sample size was based on the study by Schwartz et al. who showed significant decreases in mean post-prandial glucose in six type II diabetic subjects following ingestion of a glucose/protein shake in the presence and absence of a high dose of PI2 (1.5 g). All subjects gave informed consent before the study began, and could withdraw at any time.

Study Design

Subjects were randomly allocated to receive placebo and two of the three following doses: 7.5, 15, or 30 mg PI2 extract. On each study day subjects arrived at 8.00 AM after a 10 hour fast. They were given breakfast and 500 ml of water to drink throughout the morning, but ate nothing further until the test meal. Height and weight of all subjects were recorded during their first visit. Three and a half hours after breakfast the first blood glucose measurement was made, and subjects were given the experimental capsule and 500 ml of water. Thirty minutes later the test lunch was served. As soon as each subject completed the meal, the timing for post-prandial glucose measurements began. Subjects recorded any adverse reactions at fifteen minute intervals for 200 minutes after eating the meal.

Test Meal

On each test day subjects were fed a breakfast of granola, skim milk, and orange juice that contained 330 kilocalories derived from 67 g of carbohydrate, 2.5 g of fat, and 12 g of protein. No other food was permitted until the test meal, which was consumed at noon on the test day. The test meal was Chicken Teriyaki (Boston Market) and contained no potato products. The nutritional content of the test meal is set out in Table 1. All subjects consumed all meals in their entirety.

TABLE 1

Characteristics of the test meal

|  | Lunch Test Meal |
|---|---|
| Energy (kcal) | 460 |
| Fat (g) | 11 |
| Carbohydrate (g) | 53 |
| Protein (g) | 27 |
| Number of participants taking meal challenge after placebo | 39 |
| Average AUC for placebo participants (SD) | 2196.6 ± 1567.2 |

Glucose Measurements

Finger-prick capillary blood samples were taken 30 minutes before the test meal (Baseline), and 30, 60, 90, and 120 minutes post-prandially. Glucose measurements were made with a Dex glucometer, Model # 3952E (Bayer Pharmaceuticals), in accordance with the manufacturer's instructions.

Proteinase Inhibitor

PI2 extract was provided by Kemin Consumer Care, L.C. (Des Moines, Iowa), and was supplied in 00 gelatin capsules containing 7.5, 15, or 30 mg, respectively. A mixture of dextrose and whey protein was used to bring all capsules to a uniform weight and volume and also served as a placebo. The doses in the present study were chosen based on previous studies demonstrating efficacy at 30 mg in liquid form (Spiegel, T. A., Hubert, C. & Peikin, S. R. (1999) *University of Medicine and Dentistry of New Jersey*; Vasselli, J. R., Greenfield, D., Schwartz, L. & Heymsfield, S. B. (1999) *Obesity Research Center, St. Luke's-Roosevelt Hospital Center, Columbia University*), and 7.5 mg (Gary Green, University of Texas, San Antonio, 1996, 1997, unpublished data). The active material was produced from a single lot of potatoes (Russet Nuggets; Kemin lot 87289C, approximately 244.39 mg PI2 extract/kg).

Measurement of PI2

RP-HPLC: Formulation of the active doses was based on quantitation by high performance liquid chromatography (HPLC). Reversed-phase HPLC (RP-HPLC) analyses were performed on a Hewlett Packard Model 1100 equipped with a diode array detector using a Microsorb C-18, 5 μm particle size, 300 Angstrom pore size, 4.6×250 mm (Varian Analytical Instruments, Walnut Creek, Calif.). The chromatographic conditions were as follows: Isocratic elution for five minutes of 80% of 0.1% TFA in $H_2O$ (20% of 1% TFA in acetonitrile). Gradient from 80-30% of 0.1% TFA in $H_2O$ (20-70% of 1% TFA in acetonitrile) for 34 minutes. Gradient from 30-0% of 0.1% TFA in $H_2O$ (30-100% of 1% TFA in acetonitrile) for 4 minutes. Flow rate was 1 ml/min for all gradients, and the column temperature was maintained at 30° C. Integration of the HPLC peak area provided the relative concentration of each sample (mg/g solids).

SDS-PAGE: To further characterize the PI2 extract, samples were analyzed by gel electrophoresis. SDS gels were prepared as 4% stacking, 15% resolving with 1.5 M Tris, 0.5 M Tris, 10% SDS, 30% ammonium persulfate, TEMED, and 40% Acryl/Bis. Wells were loaded with pre-stained marker, PI2 standard, and PI2 extract. A current of 80 volts was applied for 1.5 hours. Gels were then stained with Coomasie blue staining. Pure PI2 standard was obtained by sequential RP-HPLC followed by gel filtration chromatography. Western blot using a rabbit polyclonal antibody developed by Kemin Foods, L.C. against PI2 protein, was used to further determine the identity of the major protein in the potato PI2 extract used in the current study.

Calculations and Statistical Analysis

The difference between the 30-minute post-prandial and baseline blood glucose values was calculated for each subject visit (Δ glucose). The integrated area under the blood glucose-time curve (AUC) after each test meal was calculated using the pre-meal value as the baseline, and integrating the area from 0 to approximately 120 minutes after the meal. Repeated measure analysis of variance was used to test for significant differences between areas. The research design involved repeated measures, so the PROC MIXED function in SAS was used, as this allows a more general specification of the covariance matrix of the dependent variable, and allows random factors of both the model and error terms to be correlated (Hongsen, Z. (2001) *Proceedings of the* 12th Annual Conference of the Midwest SAS Users Group, 132-140). All subjects received placebo on one visit, but only two of the three possible active treatments during the other visits, so an incomplete block design was used to evaluate the relative effectiveness of the doses. The strategy described by Wolfinger (Wolfinger, R. D. (1993) *Communications in Statistics,* *Simulation, and Computation* 22, 1079-1106) was followed to select an appropriate variance-covariance structure for the ANOVA test. The Akaike's Information Criterion was used to select the appropriate variance-covariance structure for the model. Chi-square analysis was used to evaluate data obtained as discrete variables with $p < 0.05$ considered to be significant.

Results

Figure 1B:
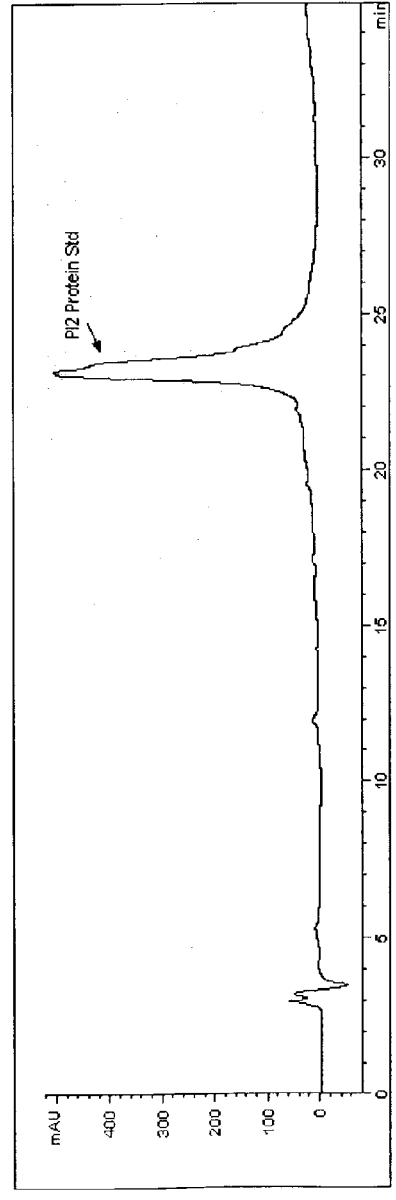
Figure 2:
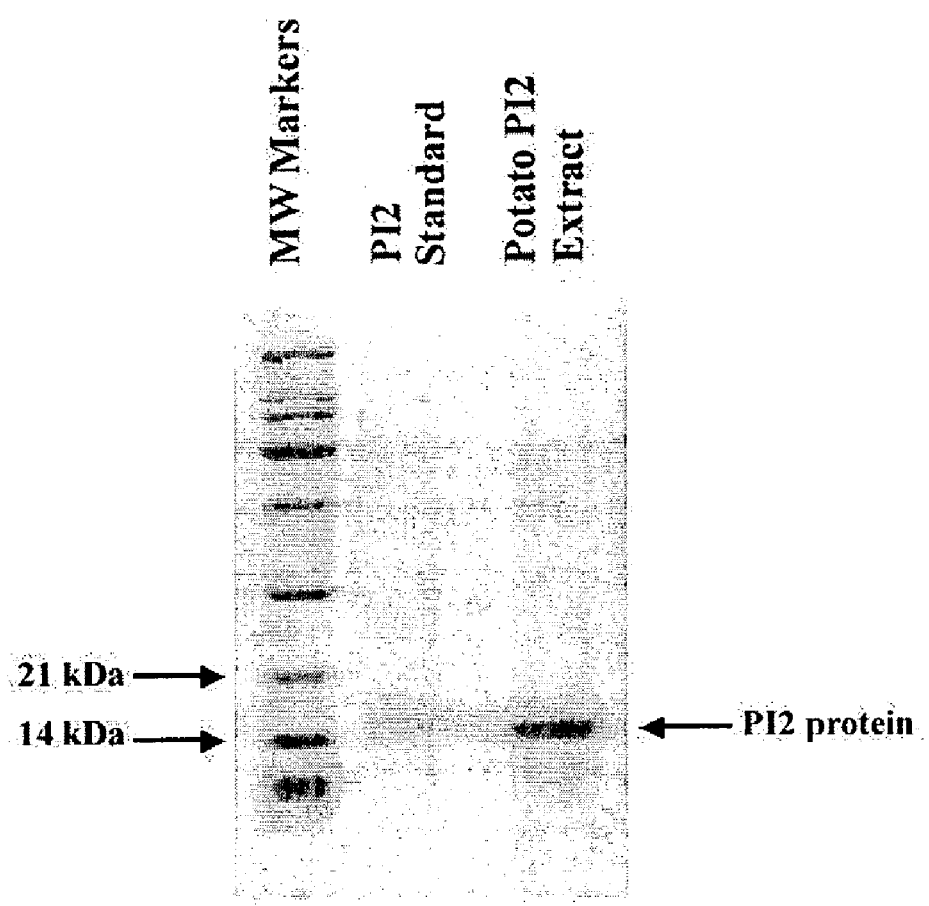
FIG. 2 is a photograph of an SDS PAGE of the potato PI2 extract used in the experiments and an authentic PI2 standard.

Doses of active PI2 extract were quantified by RP-HPLC. The integrated peak representing the PI2 extract co-eluted with a pure authentic PI2 standard, indicating that PI2 is contained in the extract and that it is the major protein (FIGS. 1*a* and 1*b*). Results of gel electrophoresis further confirm the findings of the analysis by RP-HPLC and show that the PI2 in the extract is likely present as a monomer with a molecular weight of approximately ~12 kDa (FIG. 2). MALDI MS analysis of the purified PI2 protein demonstrated that this protein has a molecular weight of 12 kDa. Western blots of the separated proteins using a rabbit polyclonal antibody for PI2 protein demonstrated that the major protein band separated by SDS-PAGE is PI2. The actual amount of PI2 protein present in a given extract could vary and ranges from 17-20%. The PI2 extract was also characterized for its trypsin and chymotrypsin inhibition activity using an in vitro assay demonstrating both trypsin and chymotrypsin inhibition. PI2 extract product contained a ratio of 0.9-1.7:1 units of trypsin: chymotrypsin inhibition activity, respectively.

Figure 3:
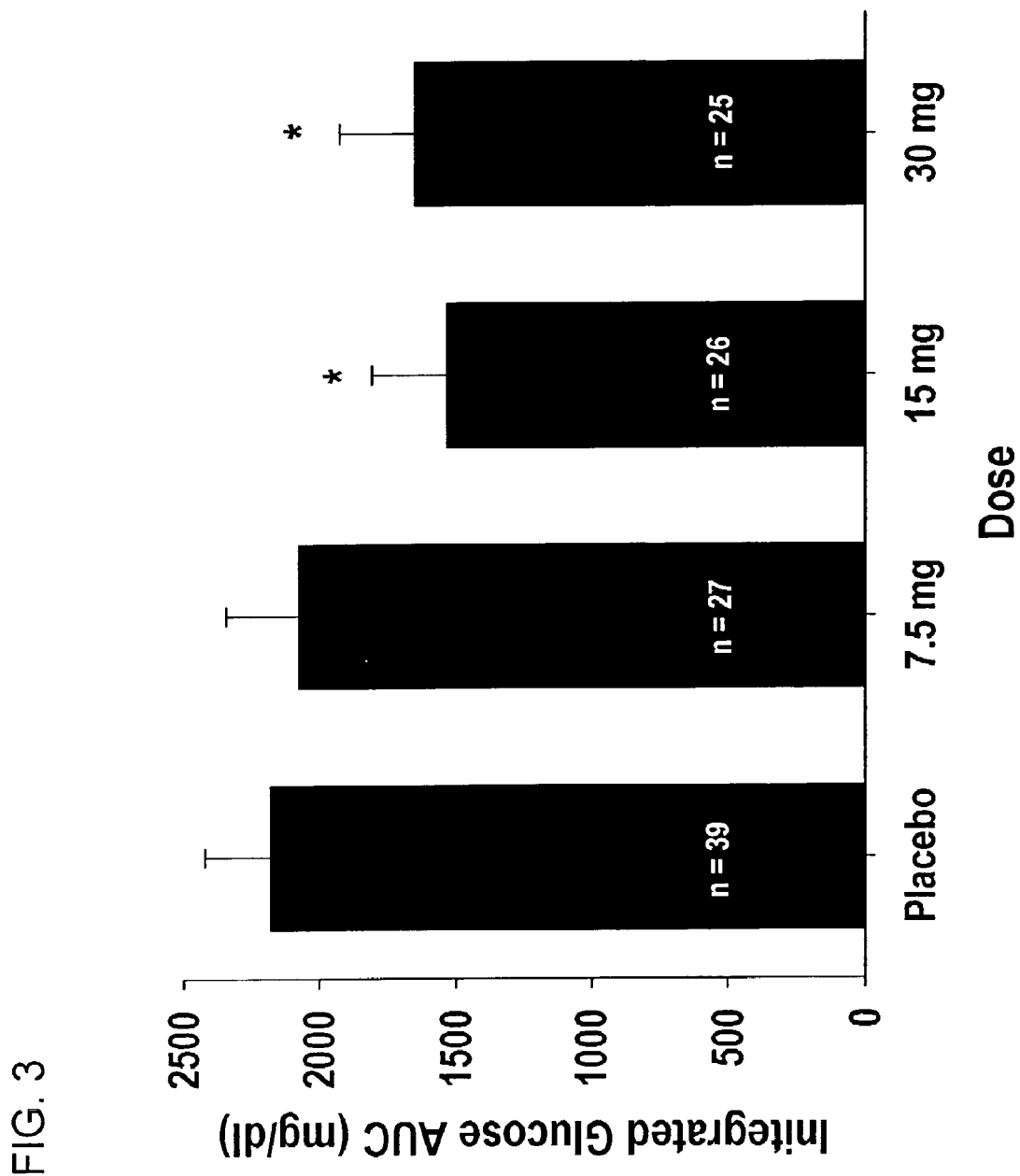
FIG. 3 is a graph showing the effect of an increasing PI2 dose on post-prandial integrated area under the blood glucose curve (AUC) after a test meal.
Figure 4:
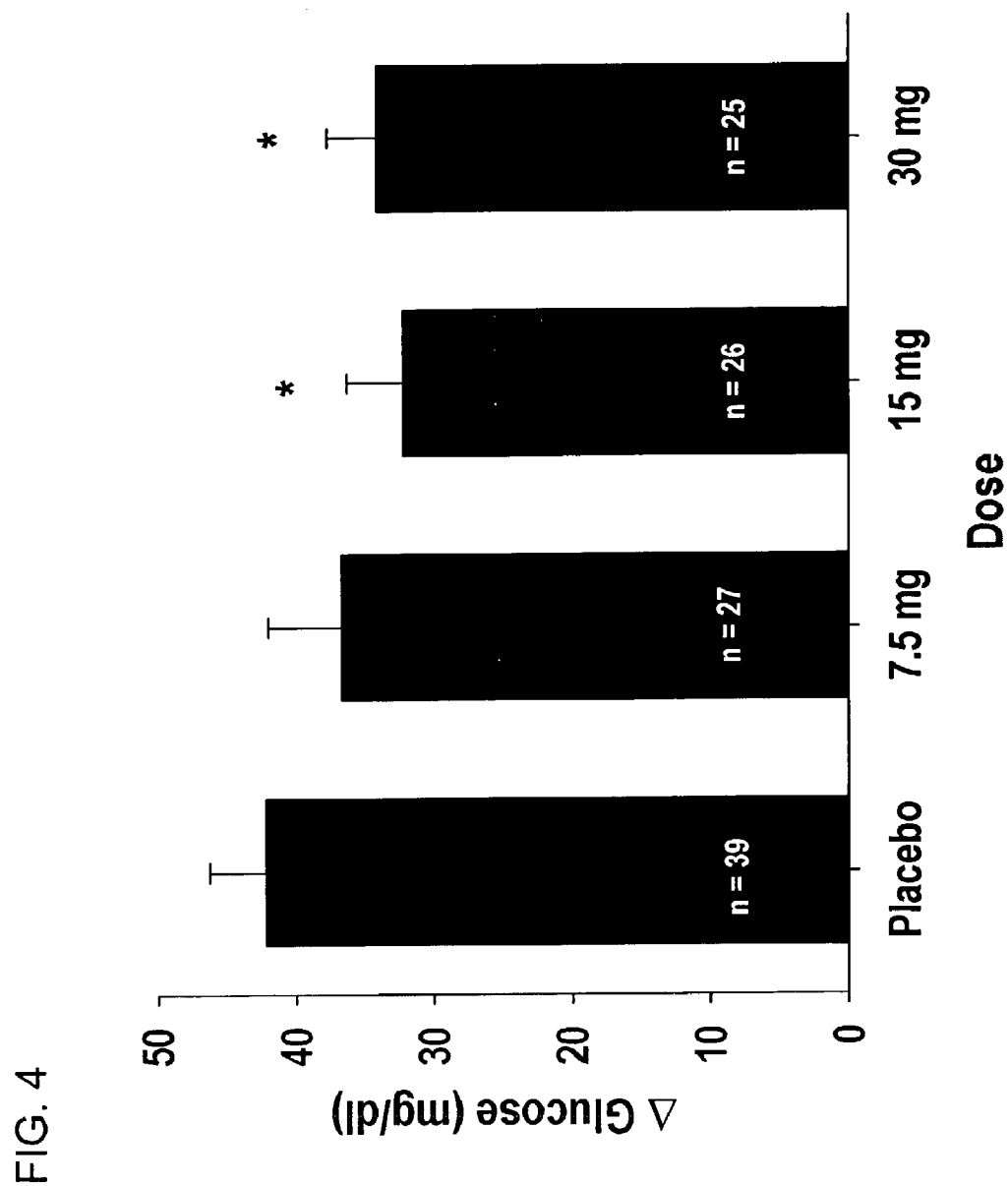
FIG. 4 is a graph showing the effect of an increasing PI2 dose on the initial rise in blood glucose above the baseline (Δ Glucose) thirty minutes after a test meal.

The volunteers in the present study consumed 120 test meals. Forty placebo doses were administered, along with 27 of each of the 7.5 mg and 15 mg doses, and 26 of the 30 mg dose, respectively (one individual declined to provide blood samples and was included in determination of adverse events monitoring). Table 1 shows the nutrient value of the test meal and the mean glucose AUC following placebo. We first examined the effect of PI2 extract on AUC; the repeated measure ANOVA model used for this analysis showed a statistically significant effect of the experimental treatment (f=3.3, p <0.05) but no statistically significant difference between the experimental blocks. Subjects given a dose of 7.5 mg PI2 extract before the test meal experienced no significant reduction in post-prandial glucose compared to placebo. The AUC of subjects receiving both 15 and 30 mg PI2 extract prior to the test meal was significantly reduced compared to placebo, but there was no significant difference in post-prandial AUC between the two higher doses (FIG. 3). The decrease in AUC for 15 and 30 mg was 29.8% and 24.5% respectively, each compared to placebo. There was a significant reduction in Δ glucose at both the 15 mg and 30 mg dose levels compared to placebo, but there was no significant difference in Δ glucose between the two higher doses (FIG. 4). The decrease in Δ glucose for the 15 and 30 mg doses was 25% and 20% respectively, each compared to placebo.

Feeding 120 test meals resulted in 14 reports of an adverse reaction from subjects. These are summarized in Table 2.

TABLE 2

Subjects recording adverse effects after eating a test meal preceded by PI2 extract

| PI2 Extract Dose (mg) | Gastrointestinal Symptoms | Headache | Total | Chi-square (vs. Placebo) |
|---|---|---|---|---|
| 0 | 3 | — | 3 | — |
| 7.5 | 5 | 1 | 6 | 0.19 |

TABLE 2-continued

Subjects recording adverse effects after eating a test meal preceded by PI2 extract

| PI2 Extract Dose (mg) | Gastrointestinal Symptoms | Headache | Total | Chi-square (vs. Placebo) |
|---|---|---|---|---|
| 15 | — | 2 | 2 | 1.76 |
| 30 | 3 | — | 3 | 0.23 |

Gastrointestinal symptoms included nausea, cramping and diarrhea. Differences in occurrence rates of adverse reactions between the treatments and the placebo were not significant (p >0.05, Chi square). Subjects experiencing symptoms rated them as mild, and frequently they were noted at only one of the recording times.

Discussion

Figure 5:
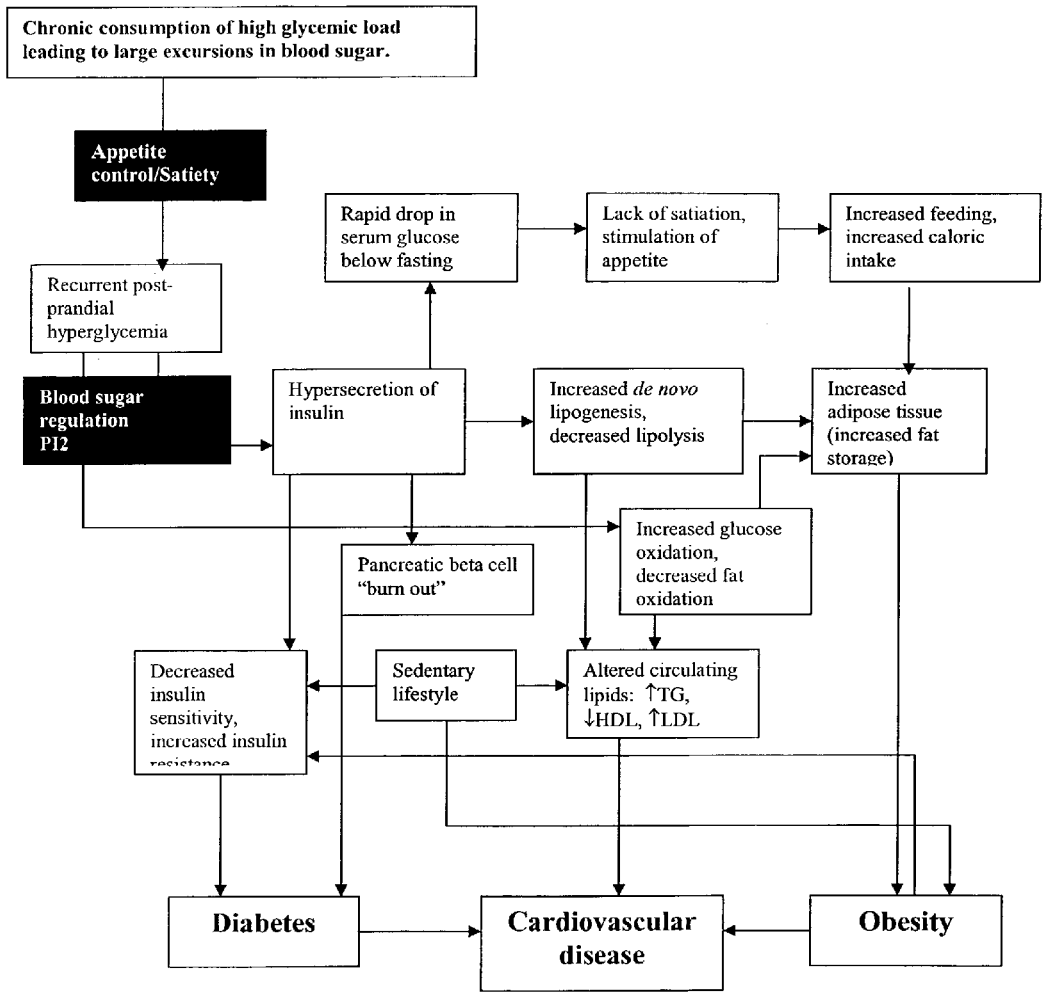
FIG. 5 is a schematic diagram of the effects of chronic consumption of a high glycemic load.

The drastic rise in obesity rates over the past 10 years has been accompanied by diets resulting in chronic glycemia and hyper secretion of insulin (Grundy; Wolever, T. M. & Bolognesi, C. (1996) *J Nutr* 126, 2807-12). This, in turn, initiates a cascade of metabolic and physiologic events resulting in decreased lipolysis, increased de novo lipogenesis, and faster onset of hunger and subsequent food intake (Jenkins; Ludwig). Rapid and drastic excursions in blood sugar may not only contribute to obesity but other chronic diseases, including diabetes and cardiovascular disease (as summarized in FIG. 5 and in Ludwig).

Accordingly, lowering the glycemic load experienced by the body by diet or other means may be an effective way to reduce the post-prandial glycemia that can lead to weight gain and obesity. Findings of the present study suggest that it is possible to lower the glycemic load experienced by the body by ingesting a supplement containing a low dose of PI2 extract prior to a meal. Doses of either 15 mg or 30 mg taken 30 minutes before a test meal significantly reduced the subsequent rise in blood glucose (FIGS. 3 and 4). A dose of 7.5 mg had no significant effect, indicating that under these test conditions the lowest effective dose lies between 7.5 and 15 mg. This study was limited to acute observations, and the effect of chronic oral administration of PI2 extract on blood sugar levels remains to be studied. However, this study is unique because PI2 has not previously been administered in solid form in an encapsulated supplement prior to the meal, and because a solid mixed meal was used for the first time. In addition, the dose used was substantially lower and less pure than that previously reported, and a larger cohort of subjects was studied. A dose of 1.5 g PI2 (90-100% pure) by column chromatography (Clarence Ryan, Washington State University, Pullman, Wash.), administered in liquid form was used in two previous studies; in one study PI2 was added to soup and fed 8 minutes before a test meal, and in the other it was incorporated in a test beverage (Hill et al.; Schwartz et al.). In neither case was it encapsulated. Other differences include the size and glycemic index of the test meals and potential variations in the PI2 dose bioactivity. We found a mean reduction in post-prandial blood glucose AUC of 29.8% with a 15 mg dose of PI2 extract and 24.5% decrease with a 30 mg active dose (FIG. 3). Schwartz et al. reported a comparable 24.5% reduction in AUC after feeding 1.5 g PI2 with a liquid glucose and protein beverage administered to diabetics. While the dose of PI2 administered in that study was apparently 100-fold larger, we cannot be sure that it was of the same specific activity as used in our current study. Therefore, it is unclear whether larger doses of PI2 extract would evoke a greater response.

Inspection of the responses of individual subjects to placebo or active dose reveals that 9 subjects experienced no reduction in glycemia with either of the two dose levels of PI2 extract administered (non-responders). There was no significant effect of BMI, age, or fasting blood glucose on responsiveness. Among the 9 non-responders from the initial study, 8 were male and one was female, although this difference was not significant (p=0.07, Chi-square).

The notion of lowering the glycemic load to reduce or maintain weight is supported by both animal and human studies. Normal rats fed isocaloric diets differing dramatically in terms of glycemic load, experience large differences in post-prandial glycemia and insulin response (Kabir, M., Rizkalla, S. W., Champ, M., Luo, J., Boillot, J., Bruzzo, F. & Slama, G. (1998) *J Nutr* 128, 35-43; Kabir, M., Rizkalla, S. W., Quignard-Boulange, A., Guerre-Millo, M., Boillot, J., Ardouin, B., Luo, J. & Slama, G. (1998) *J Nutr* 128, 1878-83). Maintaining rats on these diets for weeks at a time results in drastic differences in glucose and lipid metabolism. The levels of fatty acid synthase and de novo lipogenesis, as well as adipocyte size, are higher in rats consuming a high vs. low glycemic load diet (Kabir et al. 35-43; Kabir et al. 1878-83). These data provide evidence at the cellular and metabolic level, that drastic elevations in blood sugar caused by exposing the body to a high glycemic load results in increased fat accumulation over a relatively short window of time. Consistent with this are results from long term research showing that adult rats fed isocaloric diets evoking chronic hyperglycemia gain a significant amount of weight while those fed a diet with moderate glycemia maintain their weight (Pawlak, D. B., Denyer, G. S. & Brand-Miller, J. C. (2000) *Proc Nutr Soc Aust* 24, 215).

Weight loss studies in humans suggest that reducing the glycemia experienced by the body is an effective means to reduce and maintain weight. Subjects consuming an isocaloric diets consisting of low glycemic index foods lose more weight or maintain their relative to those consuming high glycemic index foods (Slabber, M., Barnard, H. C., Kuyl, J. M., Dannhauser, A. & Schall, R. (1994) *Am J Clin Nutr* 60, 48-53; Wolever, T. M., Jenkins, D. J., Vuksan, V., Jenkins, A. L., Wong, G. S. & Josse, R. G. (1992) *Diabetes Care* 15, 562-4; Clapp, J. R. (1997) *Arch Gynecol Obstet* 261, 101-107). These findings suggest that manipulation of the glycemic load, in these cases by consuming low glycemic load diets, can effectively stimulate weight loss and/or prevent weight gain. Combined with the results from the present study, these support the hypothesis that PI2 extract can serve as an effective nutraceutical to lower the glycemia experienced by the body, and may help promote weight loss and reduce the propensity for weight gain.

PI2 extract is proposed to exert its effect on post-prandial glucose by enhancing the release of a well characterized peptide hormone, CCK, which is naturally secreted into the blood stream by enteroendocrine cells in response to a meal (Crawley, J. N. & Corwin, R. L. (1994) *Peptides* 15, 731-55). CCK acts on various target tissues throughout the body including the gastrointestinal tract, where it delays gastric emptying leading to feelings of fullness, and the brain leading to feelings of satiety. Although not measured in the present study, previous studies in the late 1980's and 1990's demonstrated that large doses of purified PI2 enhance the release of CCK (Peikin et al.; Schwartz et al.) delay gastric emptying time (Schwartz et al.), and decrease energy intake (Hill et al.) in humans. These were followed by studies using a lower dose of less pure PI2 extract which demonstrated reduced hunger and increased fullness ratings (Spiegel et al.; Vasselli et al.) (summarized in Table 3). These findings are consistent with the well established fact that PI's are potent stimulators of CCK release in rats (Liddle).

TABLE 3

Summary of PI2 Clinical Trials

| Study | Institution | Dose | Form | Outcome |
|---|---|---|---|---|
| Spiegel et al. 1999 | Columbia University | 30 mg PI2 extract | Liquid (pre-meal shake) | Significant decrease in hunger ratings; increase in fullness ratings; 2 kg weight loss |
| Vasselli et al. 1999 | Robert Wood Johnson Medical School, University of Medicine and Dentistry of New Jersey | 30 mg PI2 extract | Liquid (pre-meal shake) | Significant decrease in hunger ratings; increase in fullness ratings |
| Schwartz et al. 1994 | University of Texas, San Antonio | 1500 mg PI2 | Liquid (shake) | Significant increase in plasma CCK; delayed gastric emptying; decreased blood sugar |
| Hill et al. 1990 | University of Leeds, U.K | 1500 mg PI2 | Liquid (pre-meal soup) | Significant decrease in food consumption |
| Peikin et al. 1987 | Robert Wood Johnson Medical School, University of Medicine and Dentistry of New Jersey | 1000 mg PI2 | Liquid (shake) | Significant increase in plasma CCK levels |
| Green, 1996–1997* | University of Texas, San Antonio | 7.5–100 mg PI2 | Liquid (shake) | Doses as low as 7.5 mg delayed gastric emptying and reduced blood sugar levels |

*Unpublished data

PI2 is a pH, heat, and salt stable protein (Bryant et al.), allowing it to be effective when administered orally, and making it unique among plant PI's. The extract used in the present study contains PI2 (FIGS. 1 and 2), and is derived from white potatoes using a method generally as described in U.S. patent application Ser. No. 09/900,555, incorporated herein by this reference. Although normally present in potatoes as a dimer, the PI2 separated from our extract appears to be in the monomeric form. The pure PI2 possess trypsin and chymotrypsin inhibition activities of 1.4 and 3.6 inhibition unites and the PI2 extract possess relative trypsin and chymotrypsin inhibition activities of 22 and 13 inhibition units. The added beneficial effect of reducing post-prandial glycemia makes PI2 extract a unique and promising nutraceutical.

Some studies involving the direct infusion of CCK have reported minor adverse side effects such as headache, nausea, and diarrhea (Crawley, J. N. & Corwin, R. L. (1994) *Peptides* 15, 731-55; Pi-Sunyer, X., Kissileff, H. R., Thornton, J. & Smith, G. P. (1982) *Physiol Behav* 29, 627-30). For this reason we questioned participants specifically about these effects which may ultimately have prompted reporting of events that would otherwise have gone un-noticed. Although there are a number of reports in the literature demonstrating morphological changes in the pancreas as a result of long term exposure to extremely high doses of natural and synthetic PI's in rodents, similar studies in pigs and primates are not associated with such effects (Struthers, B. J., MacDonald, J. R., Dahlgren, R. R. & Hopkins, D. T. (1983) *J Nutr* 113, 86-97; Harwood, J. P., Ausman, L. M., King, N. W., Sehgal, P. K., Nicolosi, R. J., Liener, I. E., Donatucci, D. & Tarcza, J. (1986) *Adv Exp Med Biol* 199, 223-37; Garthoff, L. H., Henderson, G. R., Sager, A. O., Sobotka, T. J., Gaines, D. W., O'Donnell, M. W., Jr., Chi, R., Chirtel, S. J., Barton, C. N., Brown, L. H., Hines, F. A., Solomon, T., Turkleson, J., Berry, D., Dick, H., Wilson, F. & Khan, M. A. (2002) *Food Chem Toxicol* 40, 501-16; Garthoff, L. H., Henderson, G. R., Sager, A. O., Sobotka, T. J., O'Dell, R., Thorpe, C. W., Trotter, W. J., Bruce, V. R., Dallas, H. L., Poelma, P. L., Solomon, H. M., Bier, J. W., O'Donnell, M. W., Jr., Chi, R. K., Chirtel, S. J., Barton, C. N., Brown, L. H., Frattali, V. P. & Khan, M. A. (2002) *Food Chem Toxicol* 40, 487-500). Such effects have yet to be observed in humans using PI's from natural sources. Furthermore, previous studies using PI2 have not demonstrated any side effects with doses many times that used in this study (Peikin et al.; Schwartz et al.). Side effects noted by our subjects were mild and inconsistent, and caused no withdrawals from the study. No increasing dose response was noted for any of these effects and the rate of occurrence was not different between placebo and treatment. If persistent use of PI2 extract were contemplated we may see additional mild side effects, although it is equally possible that tolerance to undesired effects would develop over time.

In conclusion, we have demonstrated in the largest randomized controlled clinical trial to date that a low dose of PI2 extract prior to a standardized meal reduces significantly post-prandial glycemia in the majority of healthy subjects. Additional studies will be required to ascertain long term effects of this supplement on blood glucose, appetite and body weight. While a mechanism of action has been proposed, it will be important to confirm this hypothesis in future studies addressing changes in serum CCK, insulin, and the like. Such studies could be instrumental in applying PI2 to the clinical problems of obesity and diabetes.

EXAMPLE 2

To better understand if the trypsin/chymotrypsin inhibiting activity of the PI2 protein was related to the glucose response to the potato proteinase inhibitor extract, a preparation that purified the PI2 fraction from the potato proteinase inhibitor extract (abbreviated pPI2) was tested along side a preparation of Bowman-Birk inhibitor after meal challenge. The Bowman-Birk inhibitor used was obtained from Sigma-Aldritch and had a stated purity of greater than 80%. Bowman-Birk inhibitor has similar enzyme inhibiting properties as pPI2. The meal challenge was conducted at a breakfast meal instead of a lunch meal, as in the prior study, and consisted of 390 kcal with 100 kcal from fat and 53 g carbohydrate and was provided to individuals who had been fasting for at least 10 hours. Each participant made two visits to the research center and underwent two meal challenges—one for the placebo and one for an active (15 mg pPI2 or 0.8 mg Bowman-Birk inhibitor) and these treatments were provided in a double-blinded format. The randomization scheme also prevented the participants or the study personnel from knowing at which visit the placebo was given until the code was broken.

In this study we found that among healthy volunteers, both pPI2 and Bowman-Birk inhibitor decreased the post-prandial glucose spike. The data is summarized in Table 4. For example ΔG was decreased by 25.5% compared to placebo among the 10 individuals taking pPI2. This difference (from a mean ΔG of 52.1 mg/dl+15.9 sd for the placebo dose versus 38.8+34.6 sd for those taking the pPI2) was evaluated by one-tailed, paired student's t test and yielded p=0.065. The Bowman-Birk inhibitor also inhibited the post-prandial glucose spike with a decrease in ΔG of 42.4%. The absolute decrease was from 47.9 mg/dl±22.6 sd for the placebo treatments compared to 27.6 mg/dl±21.6 sd for the Bowman-Birk inhibitor treatment. This was significant by student's t test with p=0.04.

Neither pPI2 nor Bowman-Birk inhibitor showed statistically significant differences in AUC, although the trend was toward absolute decreases in this parameter of 17% and 11.5% for both pPI2 and Bowman-Birk inhibitor, respectively.

In the earlier study we did discover that some individuals seemed to be unresponsive to pPI2. Again, we found this to be the case with pPI2. Three individuals were identified as non-responders with pPI2 and two individuals were unresponsive to Bowman-Birk inhibitor. A non-responder was defined as an individual who did not have a lower absolute ΔG after treatment with the active test material than with the placebo.

Thus far we are supporting the hypothesis that the PI2 protein in the potato proteinase inhibitor extract and the trypsin/chymotrypsin inhibiting activity may be related to modulation of post-prandial glucose since the relative concentration of this activity in the pPI2 showed comparable glucose modulating activity as with the original potato proteinase inhibitor extract and the Bowman-Birk inhibitor which also contains an inhibitor or inhibitors of trypsin and chymotrypsin showed glucose modulating activity.

The extraction and isolation of PI2 from potatoes begins with the addition of an organic acid, preferably formic acid, and a salt, preferably sodium chloride, to raw potatoes. The mixture is subjected to comminution to reduce the particle size of the potato particles and extract soluble proteins. Centrifugation is used to remove solids and the liquid fraction is heated at a temperature sufficient to denature many undesired proteins but not PI2. The solution is again centrifuged to remove the insoluble denatured proteins and the liquid fraction is microfiltered to remove relatively large particles. Ultrafiltration is used to remove the organic acid and salt and further purify the PI2 in the retentate.

A process for the extraction of PI2 from whole potatoes was developed in an attempt to maximize yield, minimize impurities, minimize cost, and achieve commercial feasibility. The extraction solution was evaluated based on the ability of the process to solubilize the PI2, protect the PI2 from degradation, and maximize total PI2 removed from the insoluble potato components, while minimizing the amount of co-solubilized proteins. The extraction solution incorporated the solubility and functional stability of PI2 in acidic media and at elevated temperatures. An extraction solution containing sodium chloride and formic acid has been found effective for this purpose. The ratio of extraction solution utilized to raw material extracted was minimized for cost purposes, while producing the maximum yield of PI2 per kilogram of raw potato tubers.

Reverse Phase HPLC Method

The amount of PI2, Kunitz and carboxypeptidase inhibitors was measured using reverse phase HPLC. A Microsorb C-18 column (4.6 mm x 250 mm, 5 μm particles with 300 Angstrom pore size; Varian Analytical Instruments) was used. Two mobile phase solvents were prepared, solvent A was 800 g deionized $H_2O$, 150 g acetonitrile, and 0.95 trifluoroacetic acid, and solvent B was 850 g acetonitrile and 0.85 g trifluoroacetic acid. Approximately 50 mg of the sample was added to 100 ml of solvent A. The sample was vortexed for 30 seconds, and then centrifuged at 10,000 rpm for 10 minutes. The supernatant was collected for RP-HPLC analysis. One hundred μl of the sample was injected into the column, with the pump set at 800 - 2500 psig, and a temperature of 30.0° C. The other flow rate, time, and solvent compositions are as set out in Table 5. The diode array of the detector was set at 220 nm.

TABLE 4

Comparison of purified PI2 and Bowman-Birk Inhibitor on ΔG and AUC

| Parameter | | Purified PI2 Product | | Bowman-Birk Inhibitor | |
| --- | --- | --- | --- | --- | --- |
| | | Placebo | Active | Placebo | Active |
| Mean ΔG ± SD | Study 1 | 52.1 ± 15.9 | 38.8 ± 34.6<br>*p = 0.065 | 47.9 ± 22.6 | 27.6 ± 21.6<br>*p = 0.04 |
| Mean ΔG ± SD | Study 2 | 55.1 ± 21.3 | 45.7 ± 21.7<br>*p = 0.058 | 49.8 ± 13.9 | 45 ± 21.8<br>*p > 0.05 |
| Mean AUC ± SD | Study 1 | 2279 ± 1187 | 2747 ± 1325<br>*p = 0.15 | 2015 ± 1702 | 1783 ± 1935<br>*p = 0.32 |
| Mean AUC ± SD | Study 2 | 2496.9 ± 1878.1 | 2153.6 ± 2181.3<br>*p = 0.229 | | |

*one tailed paired t test (versus placebo)

TABLE 5

HPLC Conditions

| Time (min) | Flow rate (ml/min) | Solvent Composition (volume %) |
|---|---|---|
| 0 | 1 | 100% A |
| 5 | 1 | 100% A |
| 34 | 1 | 38% A |
| 38 | 1 | 100% B |
| 40 | 2 | 100% B |
| 45 | 2 | 100% B |
| 50 | 1 | 100% A |
| 55 | 1 | 100% A |

An external standard was prepared to construct a standard curve for calibration of the column. Five mg of BSA were dissolved in 10 ml of solvent A. Four volumes, i.e., 25, 50, 75, and 100 µl, were injected into the column. A calibration curve was generated from the results.

EXAMPLE 3

Five hundred grams of potato tubers were extracted with 213 ml of 1% formic acid solution in a Waring blender for 2.5 minutes. The slurry was centrifuged at 10,000 rpm for 40 minutes. The liquid was decanted and filtered through #4 Whatman filter paper, yielding 486 g of clarified extract. Fifty grams of this clarified extract was poured into each of six 125 ml Erlenmeyer flasks equipped with magnetic stir bars. The amount of NaCl corresponding to Table 6 was added to each flack and stirred until the salt was dissolved. The flasks were then heated on high with stirring on a hot plate until the temperature of the extract reached 70° C. After ambient cooling to room temperature, the solutions were centrifuged at 12,000 rpm for 5 minutes and then analyzed using the above-described reverse phase HPLC method. The reported level of PI2 was calculated by integrating the area of the PI2 peak. The injection volume was 100 µl and the following equation was used to equate peak areas to protein levels:

$$\text{Protein (mg/ml)} = \left[\left(\frac{\text{peak area}}{4}\right) \times 8.17 \times 10^{-5}\right] + 0.0338$$

To clarified potato extract was added varying amounts of sodium chloride, followed by heating to 70° C. for 10 minutes. After cooling to room temperature, the solutions were analyzed for the protein eluting after PI2 in the HPLC method for PI2 quantification. The results are shown in Table 6.

TABLE 6

Protein Removal with Varying Sodium Chloride Levels

| [NaCl] N | Protein Eluting at 16-30 minutes mg/ml | Protein Eluting at ~23-30 minutes mg/ml | PI2 Level mg/ml |
|---|---|---|---|
| 0.0 | 0.504 | 0.378 | 0.167 |
| 0.1 | 0.298 | 0.184 | 0.160 |
| 0.2 | 0.245 | 0.141 | 0.172 |
| 0.3 | 0.178 | 0.076 | 0.149 |
| 0.4 | 0.150 | 0.071 | 0.169 |
| 0.5 | 0.119 | 0.076 | 0.189 |

To establish the removal of Kunitz impurities from the potato extract, which have been shown to diminish the effectiveness of PI2 to increase satiety, the reverse phase HPLC method was used on a commercially available Kunitz standard purchased from SIGMA. A chromatograph of the Kunitz standard revealed that the major peak of the Kunitz impurities appears at approximately 25 minutes. Another inhibitor known to be present in potatoes is the carboxypeptidase inhibitor. The reverse phase HPLC method was used on a commercially available carboxypeptidase standard purchased from SIGMA. A chromatograph of the carboxypeptidase standard revealed that the major peaks of the carboxypeptidase impurities is a doublet that appears at approximately 17 minutes. At a level of 0.3 N sodium chloride and above, the post heat-treatment protein level remains relatively constant. The amount of PI2 remained relatively constant for all trials, indicating that at 70° C. no PI2 is precipitated at the salt levels up to 0.5 N. In order to reach the level of NaCl required in the heat-treatment phase, it is necessary to use an extractant with approximately 2 times the desired final salt concentration. Accordingly, a salt level of at least 0.3 N is desirable in the extraction solution during heat treatment at 70° C. to ensure efficient removal of Kunitz type proteins. Purity of the final PI2 product can be improved with greater amounts of sodium chloride.

EXAMPLE 4

An optimization study was performed to determine both the proper NaCl content and formic acid content of the extraction solution. The ideal extraction solution formulation would maximize the amount of PI2 liberated from the potato matrix, while minimizing the amount of protein contaminants solubilized. The liberation of PI2 was measured as yield, normalized to an extraction solution composition of 1.0 N NaCl. This was chosen as the normalization basis due to the previously stated prediction necessitating a two-fold increase of NaCl beyond the 0.5 N system shown effective for impurity removal in the heat-treatment stage. For optimization purposes, PI2 protein purity was measured and compared empirically to the normalized extraction yields. Extraction solutions containing NaCl concentrations from 0.0 N to 2.0 N were examined. In a similar manner, the formic acid content of the extraction solution was optimized. Formic acid contents ranging from 0.0 percent to 2.5 percent were studied.

TABLE 7

Sodium Chloride Optimization Data

| [NaCl] N | PI2 Area | Doublet Area | Time (min) | "Kunitz" Area | Time (min) |
|---|---|---|---|---|---|
| 0.0 | 4283.0 | 6402.2 | 17.28 | 83436.8 | ~23.5-29.0 |
| 1.0 | 6627.8 | 6294.6 | 17.28 | 131502.6 | ~23.5-29.0 |
| 1.0 | 4771.1 | 5571.2 | 16.97 | 113666.7 | ~23.5-29.0 |
| 2.0 | 5146.2 | 5306.3 | 16.95 | 120910.1 | ~23.5-29.0 |
| 0.0 | 4712.6 | 6231.8 | 17.48 | 83908.4 | ~23.5-29.0 |
| 0.5 | 6592.7 | 6932.0 | 17.48 | 125256.4 | ~23.5-29.0 |
| 1.0 | 7578.4 | 7425.0 | 17.47 | 128660.5 | ~23.5-29.0 |
| 2.0 | 6822.6 | 6890.4 | 17.46 | 130632.2 | ~23.5-29.0 |
| 0.0 | 4235.2 | 6130.1 | 17.74 | 90357.4 | ~24.0-29.5 |
| 0.7 | 5964.6 | 6606.2 | 17.72 | 135932.2 | ~24.0-29.5 |
| 1.0 | 6746.7 | 6531.5 | 17.50 | 126617.3 | ~23.5-29.0 |
| 1.3 | 6062.5 | 6163.9 | 17.69 | 142488.8 | ~24.0-29.5 |
| 0.0 | 4699.6 | 6065.3 | 17.54 | 89125.2 | ~23.75-29.25 |
| 1.0 | 7768.5 | 6008.5 | 17.54 | 138907.2 | ~23.75-29.25 |
| 1.3 | 8095.2 | 6513.1 | 17.54 | 151858.8 | ~23.75-29.25 |
| 0.0 | 4743.7 | 5563.6 | 17.70 | 80937.5 | ~24.0-29.5 |
| 0.5 | 5825.3 | 5577.7 | 17.69 | 120352.4 | ~24.0-29.5 |
| 1.0 | 6848.1 | 5260.6 | 17.75 | 129407.5 | ~24.0-29.5 |
| 1.3 | 7173.2 | 5365.8 | 17.53 | 142758.6 | ~24.0-29.5 |

TABLE 8

Sodium Chloride Optimization Data Continued

| [NaCl] N | PI2 Area | PI2 (mg/ml) | Doublet Area | Protein (mg/ml) | "Kunitz" Area | Protein (mg/ml) |
|---|---|---|---|---|---|---|
| 0.0 | 4283.0 | 0.16 | 6402.2 | 0.20 | 83436.8 | 1.73 |
| 1.0 | 6627.8 | 0.21 | 6294.6 | 0.20 | 131502.6 | 2.68 |
| 1.0 | 4771.1 | 0.17 | 5571.2 | 0.19 | 113666.7 | 2.32 |
| 2.0 | 5146.2 | 0.18 | 5306.3 | 0.18 | 120910.1 | 2.47 |
| 0.0 | 4712.8 | 0.17 | 6231.8 | 0.20 | 83908.4 | 1.73 |
| 0.5 | 6592.7 | 0.21 | 6932.0 | 0.21 | 125256.4 | 2.55 |
| 1.0 | 7578.4 | 0.23 | 7425.0 | 0.22 | 128660.5 | 2.62 |
| 2.0 | 6822.6 | 0.21 | 6890.4 | 0.21 | 130632.2 | 2.66 |
| 0.0 | 4235.2 | 0.16 | 6130.1 | 0.20 | 90357.4 | 1.86 |
| 0.7 | 5964.6 | 0.19 | 6606.2 | 0.21 | 135932.2 | 2.76 |
| 1.0 | 6746.7 | 0.21 | 6531.5 | 0.20 | 126617.3 | 2.58 |
| 1.3 | 6062.5 | 0.20 | 6163.9 | 0.20 | 142488.8 | 2.89 |
| 0.0 | 4699.6 | 0.17 | 6065.3 | 0.20 | 89125.2 | 1.84 |
| 1.0 | 7768.5 | 0.23 | 6008.5 | 0.19 | 138907.2 | 2.82 |
| 1.3 | 8095.2 | 0.24 | 6513.1 | 0.20 | 151858.8 | 3.08 |
| 0.0 | 4743.7 | 0.17 | 5563.6 | 0.19 | 80937.5 | 1.68 |
| 0.5 | 5825.3 | 0.19 | 5577.7 | 0.19 | 120352.4 | 2.46 |
| 1.0 | 6848.1 | 0.21 | 5260.6 | 0.18 | 129407.5 | 2.63 |
| 1.3 | 7173.2 | 0.22 | 5365.8 | 0.18 | 142758.6 | 2.90 |

TABLE 9

Sodium Chloride Optimization Data Continued

| [NaCl] N | PI2 (mg/ml) | PI2 mg | Normalized yield | Doublet (mg/ml) | Doublet (mg) | Kunitz (mg/ml) | Total Kunitz (mg) | Purity |
|---|---|---|---|---|---|---|---|---|
| 0.0 | 0.16 | 78.25 | 77.51% | 0.20 | 98.76 | 1.73 | 844.50 | 7.66% |
| 1.0 | 0.21 | 100.75 | 100.00% | 0.20 | 97.53 | 2.68 | 1307.21 | 6.69% |
| 1.0 | 0.17 | 79.59 | 100.00% | 0.19 | 87.02 | 2.32 | 1090.74 | 6.33% |
| 2.0 | 0.18 | 82.23 | 104.38% | 0.18 | 83.70 | 2.47 | 1146.21 | 6.27% |
| 0.0 | 0.17 | 81.88 | 74.82% | 0.20 | 96.49 | 1.73 | 843.57 | 8.01% |
| 0.5 | 0.21 | 100.78 | 91.34% | 0.21 | 104.07 | 2.55 | 1251.43 | 6.92% |
| 1.0 | 0.23 | 104.63 | 100.00% | 0.22 | 103.22 | 2.62 | 1218.05 | 7.34% |
| 2.0 | 0.21 | 97.11 | 93.36% | 0.21 | 97.73 | 2.66 | 1228.97 | 6.82% |
| 0.0 | 0.16 | 72.99 | 82.29% | 0.20 | 90.21 | 1.86 | 855.33 | 7.17% |
| 0.7 | 0.19 | 88.27 | 92.58% | 0.21 | 94.07 | 2.76 | 1263.08 | 6.11% |
| 1.0 | 0.21 | 100.78 | 100.00% | 0.20 | 98.72 | 2.58 | 1246.21 | 6.97% |
| 1.3 | 0.20 | 93.49 | 93.51% | 0.20 | 94.45 | 2.89 | 1386.67 | 5.94% |
| 0.0 | 0.17 | 80.77 | 73.47% | 0.20 | 93.75 | 1.84 | 883.03 | 7.64% |
| 1.0 | 0.23 | 111.08 | 100.00% | 0.19 | 94.18 | 2.82 | 1370.31 | 7.05% |
| 1.3 | 0.24 | 113.59 | 102.82% | 0.20 | 98.48 | 3.08 | 1486.42 | 6.69% |
| 0.0 | 0.17 | 80.41 | 80.24% | 0.19 | 88.13 | 1.68 | 797.53 | 8.32% |
| 0.5 | 0.19 | 92.04 | 90.39% | 0.19 | 89.68 | 2.46 | 1187.23 | 6.72% |
| 1.0 | 0.21 | 100.96 | 100.00% | 0.18 | 85.91 | 2.63 | 1263.04 | 6.96% |
| 1.3 | 0.22 | 99.55 | 103.05% | 0.18 | 83.15 | 2.90 | 1329.54 | 6.58% |

TABLE 10

Average Normalized Yields and Purities With Varying NaCl

| NaCl Normality | Average Yield | Average Purity |
|---|---|---|
| 0.0 | 77.67% | 7.76% |
| 0.5 | 90.87% | 6.82% |
| 0.7 | 92.58% | 6.11% |
| 1.0 | 100.00% | 6.89% |
| 1.3 | 99.80% | 6.40% |
| 2.0 | 98.87% | 6.54% |

While NaCl normalities of 0.5 N and above were seen to give high yields, a normality of 1.0 N was selected as maximizing both yield and purity.

TABLE 11

Formic Acid Optimization Data

| Formic acid conc. | PI2 Area | Impurity Peak Area | Time (min) | Doublet Area | Time (min) | "Kunitz" Area | Time (min) |
|---|---|---|---|---|---|---|---|
| 0.0% | 7483.6 | 2453.50 | 15.63 | 6848.6 | 17.56 | 225054.1 | ~23.75-31.0 |
| 1.5% | 7768.5 | 797.67 | 15.73 | 6008.5 | 17.54 | 138907.2 | ~23.75-29.25 |
| 0.1% | 8252.0 | 2867.90 | 15.59 | 7071.5 | 17.54 | 226680.4 | ~23.75-30.5 |
| 0.5% | 7165.9 | 2071.70 | 15.65 | 6198.6 | 17.53 | 203839.7 | ~23.75-30.5 |
| 1.0% | 8353.7 | 813.80 | 15.61 | 5873.0 | 17.50 | 161433.2 | ~23.75-29.25 |
| 1.5% | 7939.3 | 893.50 | 15.64 | 5979.0 | 17.54 | 135420.3 | ~23.75-29.25 |
| 0.1% | 7005.0 | 1805.90 | 14.85 | 7788.5 | 17.00 | 233105.7 | ~23.25-30.0 |
| 1.5% | 7407.2 | 962.20 | 15.10 | 6109.7 | 16.98 | 144764.2 | ~23.5-29.0 |

TABLE 11-continued

Formic Acid Optimization Data

| Formic acid conc. | PI2 Area | Impurity Peak Area | Time (min) | Doublet Area | Time (min) | "Kunitz" Area | Time (min) |
|---|---|---|---|---|---|---|---|
| 2.0% | 7116.2 | 1117.55 | 15.11 | 6441.2 | 16.97 | 187670.8 | ~23.25-30.0 |
| 2.5% | 7318.8 | 1176.40 | 15.07 | 6649.6 | 16.97 | 180476.2 | ~23.25-30.0 |

TABLE 12

Formic Acid Optimization Data

| Formic acid conc. | PI2 Area | PI2 (mg/ml) | Impurity Peak Area | Protein (mg/ml) | Doublet Area | Protein (mg/ml) | "Kunitz" Area | Protein (mg/ml) |
|---|---|---|---|---|---|---|---|---|
| 0.0% | 7483.6 | 0.19 | 2453.50 | 0.09 | 6848.6 | 0.17 | 225054.1 | 4.37 |
| 1.5% | 7768.5 | 0.23 | 797.67 | 0.09 | 6008.5 | 0.19 | 138907.2 | 2.82 |
| 0.1% | 8252.0 | 0.20 | 2867.90 | 0.10 | 7071.5 | 0.18 | 226680.4 | 4.40 |
| 0.5% | 7165.9 | 0.18 | 2071.70 | 0.08 | 6198.6 | 0.16 | 203839.7 | 3.96 |
| 1.0% | 8353.7 | 0.20 | 813.80 | 0.06 | 5873.0 | 0.16 | 161433.2 | 3.15 |
| 1.5% | 7939.3 | 0.19 | 893.50 | 0.06 | 5979.0 | 0.16 | 135420.3 | 2.65 |
| 0.1% | 7005.0 | 0.18 | 1805.90 | 0.08 | 7788.5 | 0.19 | 233105.7 | 4.53 |
| 1.5% | 7407.2 | 0.18 | 962.20 | 0.06 | 6109.7 | 0.16 | 144764.2 | 2.83 |
| 2.0% | 7116.2 | 0.18 | 1117.55 | 0.06 | 6441.2 | 0.17 | 187670.8 | 3.65 |
| 2.5% | 7318.8 | 0.18 | 1176.40 | 0.06 | 6649.6 | 0.17 | 180476.2 | 3.52 |

TABLE 13

Formic Acid Optimization Data

| Formic acid conc. | PI2 (mg/ml) | PI2 mg | Imp. (mg/ml) | Impurity mg | Doublet (mg/ml) | Doublet mg | "Kunitz" (mg/ml) | "Kunitz" mg | Yield | Purity |
|---|---|---|---|---|---|---|---|---|---|---|
| 0.0% | 0.19 | 88.80 | 0.09 | 42.64 | 0.17 | 82.97 | 4.37 | 2085.22 | 79.93% | 3.86% |
| 1.5% | 0.23 | 111.08 | 0.09 | 44.15 | 0.19 | 94.18 | 2.82 | 1370.31 | 100.00% | 6.86% |
| 0.1% | 0.20 | 98.57 | 0.10 | 47.76 | 0.18 | 87.43 | 4.40 | 2159.78 | 104.57% | 4.12% |
| 0.5% | 0.18 | 85.43 | 0.08 | 38.93 | 0.16 | 76.60 | 3.96 | 1880.60 | 90.63% | 4.10% |
| 1.0% | 0.20 | 94.56 | 0.06 | 28.10 | 0.16 | 75.38 | 3.15 | 1529.05 | 100.56% | 5.69% |
| 1.5% | 0.19 | 94.26 | 0.06 | 28.71 | 0.16 | 76.02 | 2.65 | 1280.14 | 100.00% | 6.37% |
| 0.1% | 0.18 | 88.79 | 0.08 | 38.60 | 0.19 | 96.35 | 4.53 | 2271.21 | 96.55% | 3.56% |
| 1.5% | 0.18 | 91.96 | 0.06 | 30.23 | 0.16 | 79.53 | 2.83 | 1407.70 | 100.00% | 5.71% |
| 2.0% | 0.18 | 88.75 | 0.06 | 31.56 | 0.17 | 82.31 | 3.65 | 1809.93 | 96.50% | 4.41% |
| 2.5% | 0.18 | 88.56 | 0.06 | 31.37 | 0.17 | 82.33 | 3.52 | 1700.64 | 96.30% | 4.65% |

TABLE 14

Average Normalized Yields and Purities With Varying Formic Acid

| % Formic acid | Average yield | Average purity |
|---|---|---|
| 0.0 | 79.93% | 3.86% |
| 0.1 | 100.56% | 3.84% |
| 0.5 | 90.63% | 4.10% |
| 1.0 | 100.56% | 5.69% |
| 1.5 | 100.00% | 6.31% |
| 2.0 | 96.50% | 4.41% |
| 2.5 | 96.30% | 4.65% |

TABLE 15

Average Normalized PI2 Yield and Liquid Yield With Varying Extraction Ratio

| Extraction ratio | Normalized, Average Yield | Average Yield in mg/kg |
|---|---|---|
| 0.1 | 22.38% | 24.07 |
| 0.2 | 60.47% | 64.94 |
| 0.3 | 85.56% | 91.98 |
| 0.4 | 100.00% | 107.32 |
| 0.5 | 100.42% | 107.76 |
| 0.6 | 101.03% | 108.49 |
| 0.7 | 100.42% | 107.74 |
| 0.8 | 100.74% | 108.09 |
| 0.9 | 101.21% | 108.57 |
| 1.0 | 101.38% | 108.81 |

The data indicate the use of 1.5% formic acid content for the extraction solution. While other formic acid concentrations offer similar yield, 1.5% formic acid content clearly maximizes purity.

EXAMPLE 5

An experiment was conducted to determine the effect on yield by using varying amounts of the extraction solution comprised of 1.5% formic acid and 1.0 N NaCl in water. The weight ratio of potatoes to extraction solution was varied from 1:1 to 1:10. The ratios used and the observed yields are reported in Table 15.

While the highest yield is achieved with the highest ratio of extraction solution, the gain in total yield is minimal above the 0.4 to one ratio (1:2.5 w/w extraction solution to potatoes, respectively). This ratio has been selected, in order to minimize extraction solution cost and material handling concerns, such as heating, cooling and evaporation.

The data dictate the choice of approximately 1.0 N sodium chloride as the preferred concentration in the extraction solution for the isolation of PI2. Using 1.0 N sodium chloride results in maximized yield of PI2 under the tested conditions, and although other concentrations are capable of producing similar yields, the PI2 protein purity that is represented by the use of 1.0 N NaCl is maximized at 1.0 N. Higher PI2 protein purity could be achieved by using less sodium chloride, however this would result in a reduced PI2 yield. This level of sodium chloride is also appropriate for the removal of the Kunitz type impurities. Similarly, the data dictate the selection of 1.5% formic acid as the preferred concentration for the extraction of PI2. An extraction solution that contains 1.5% formic acid exhibits beneficial antimicrobial and anti-proteolytic behavior. The yield of PI2 is maximized under the tested conditions at 1.5% formic acid content in the extraction solution, and this concentration also provides the highest PI2/Kunitz purity of the formulations that attain comparable yields. There is no significant increase in total yield when creating a slurry that is composed of greater than thirty percent extraction solution by weight. A slurry of thirty percent extraction solution composition is roughly equivalent to a one-part extraction solution to two and one-half parts raw material (1:2.5 solvent:solid ratio).

EXAMPLE 6

A liquid extraction solution containing approximately 1.0 N sodium chloride and 1.5% formic acid was found to be effective in solubilizing PI2 while retaining its functional stability. The extraction system was examined to optimize the release of the target protein from the potato cellular matrix. Physical grinding is necessary to rupture the potato tuber cells and thereby release the protein into the liquid phase. The final grind profile of the potato slurry was examined for complete release of soluble proteins into liquid phase, minimal PI2 degradation, and ease of liquid/solid separation. Grind profile and extraction efficiency correlations were examined, followed by separation ease of the optimized grind profile.

A set of stackable sieves conforming to ASTM specification 11 is assembled with the largest sieve size on top and the rest placed in descending sieve size. The sieve size range should be chosen so as to capture at least 95% of the solids in the suspension to be sized. Approximately 250 grams of the suspension to be sized is poured onto the top of the sieve stack. The top sieve is washed repeatedly with water until no more solids appear to be passing through the sieve. This sieve is then removed and this washing repeated for each sieve. The contents of each sieve are placed in pre-weighed weigh boats and placed in a vacuum oven at less than 100° C., but more than 50° C., to dry for at least 12 hours. After the solids are dry their weights are measured on an analytical balance and recorded. The particle size distribution is reported as the dry weight of the solids retained on each sieve expressed as a percentage of total dry solids retained. Results are reported in Table 16 using micrometers as the size unit.

TABLE 16

Sample Size Distribution Report

| Particle Size μ (micrometers) | % Solids Retained |
|---|---|
| 1170 | 11 |
| 1080 | 32 |
| 625 | 38 |
| 400 | 19 |

For these trials whole, raw potatoes were extracted using an aqueous solution of 1.5% formic acid and 1.0 N NaCl in a weight ratio of 1:2.5 extraction solution to potatoes. PI2 concentration was derived using reverse phase HPLC method described previously.

The degree of disintegration of the potato in the presence of the extraction solution has been studied. To test this aspect of the extraction, samples of the optimized extraction solution and whole, raw potatoes were ground using commercially available Commitrol grinders. The test protocol was designed to determine the grinding device's ability to generate to a number of consistent target profiles, and examine the particle size distribution within these grinds. The experimentally ground slurries were analyzed for PI2 content. A trend was discovered in which a finer grind profile exhibited increased yield of PI2 on a mg/kg basis. Extractions with an average particle size of greater than 1000 μm showed a marked diminution of PI2 extraction efficacy.

When ground on a Urschel grinder to a nominal particle size of less than 100 μm, the samples yielded 85 mg PI2 per kg of potato. A similar test done using the same lot of potatoes and extractive solution using a Hobart grinder giving a grind size of approximately 1500 μm afforded 70 mg PI2 per kg of potato.

TABLE 17

Comparison of Coarse and Fine Grind Processes

| Grinder | Potatoes (kg) | Extraction solution | Average particle size-μm (micrometers) | Total slurry (kg) | PI2 mg/kg potato |
|---|---|---|---|---|---|
| Hobart Coarse | 5.59 | 2.24 | ~1500 | 7.83 | 70 |
| Urschel Fine | 5.72 | 2.29 | <90 | 11.03 | 85 |

There was not an appreciable difference of ease of filtration under the conditions adopted for this experiment. The final pulp recovered from the Urschel grind was 17.3% by weight of the slurry and contained a moisture level of 49.8%. The pulp recovered from the Hobart grind was 31.9% by weight of the slurry and contained a moisture level of 60.5%. This represents a potential loss in yield of approximately 10 percent in the more coarse grind profile, using a liquid yield weight percentage (7.1% residual liquid in the finely ground waste solids as opposed to 17.2% residual liquid in the coarsely ground waste solids).

In addition to PI2 and mass balance losses, the finer grind does exhibit a greater amount of total protein extracted using the finer grind protocol. The resulting liquid extracts were assayed using the reverse phase HPLC method. The fine grind extract does contain a greater concentration of undesirable proteins. In particular, the PI2/Kunitz purity (taken as the concentration of PI2 divided by the total concentration of the Kunitz impurities and the PI2) decreases from 7.41 percent purity for the coarse grind and 5.99 percent purity in the extract resulting from the fine grind.

A further study examined the yield of PI2 using a variety of grind profiles. The grind profiles examined varied from 300 μm average particle size to 1200 μm average particle size.

TABLE 18

Optimization of Grinding Profile and PI2 Yield

| Average grind profile | Gap | PI2 yield | Kunitz content | PI2/'Kunitz' purity | Temperature increase |
|---|---|---|---|---|---|
| Approx. 300 micron | 214μ | 98.55% | 105.77% | 48.23% | 13.1° C. |
| Approx. 500 micron | 388μ | 100.00% | 100.00% | 50.00% | 10.4° C. |
| Approx. 700 micron | 633μ | 93.68% | 97.94% | 48.89% | 8.8° C. |
| Approx. 900 micron | 968μ | 91.32% | 94.88% | 49.05% | 6.7° C. |

TABLE 18-continued

Optimization of Grinding Profile and PI2 Yield

| Average grind profile | Gap | PI2 yield | Kunitz content | PI2/ 'Kunitz' purity | Temperature increase |
|---|---|---|---|---|---|
| Approx. 1200 micron | 1519μ | 86.57% | 84.97% | 50.47% | 5.2° C. |

Table 18 presents the optimization study for final grind profile with respect to PI2 yield. The yields and purities are normalized to the highest PI2 yield in the sample set. The highest yield was observed at approximately 500 μm average particle size. The PI2 /Kunitz purity is also acceptable, only one other grind profile exhibited a higher purity, however with an unacceptable sacrifice in PI2 yield. In order to produce the desired grind profile at the pilot scale, a "Microcut Head Assembly" was used. The final grind profile is determined by several mechanical characteristics of the grinding head, such as the number, spacing and angle of blades in the head as well as the speed and type of impeller. The Microcut head features 190 tungsten carbide blades, each .084 inches thick. This thickness allows for a spacing of .0153 inches (388.62 μ) between each blade. The product is pushed through the spaces between the blades by the impeller. The impeller being used is a "veri-cut" due to its durability and the uniform particle size it produces. This impeller, in conjunction with this head assembly, produces a depth of cut of .0016 inches (40.64 μ). The interaction of the impeller, grinding blades and raw materials generates the friction responsible for the observed temperature rise. A rise of ten degrees was not considered harmful, due to the heat stability of PI2 (70° C. for more than 3 hours). The depth of cut may vary slightly with the speed of the impeller, which is determined by the motor. For these studies, a consistent grind profile was used to provide an average particle size of approximately 500 μ.

Trials were then conducted, using the optimized grind profile, to determine the proper separation conditions of the liquid/solid slurry. There are many techniques available to separate solids from liquids. A basket type centrifuge was identified as appropriate for the separation of potato solids from the extraction solution mixture. The target goals for the separation process were to maximize the liquid extracted from the slurry, while generating a cake with a minimized moisture content. As the PI2 is expected to disperse within the liquid fraction, maximizing liquid recovery is of primary importance to maximizing the yield of PI2 . Pilot trials were performed, using a pilot model that would be directly scaleable to a full production model. The characteristic of the centrifuge that was optimized by these trials was the filter-mesh screen size.

TABLE 19

Screen Mesh Trial for Optimization

| Mesh size | Liquid recovery | Solid moisture content | Suspended solid | Time per L collected |
|---|---|---|---|---|
| 100μ | 100.00% | 5.35% | 5.35% | 0.972 L/min |
| 75μ | 99.87% | 5.78% | 4.55% | 0.968 L/min |
| 50μ | 99.54% | 5.94% | 1.05% | 0.967 L/min |
| 35μ | 99.13% | 6.05% | 0.25% | 0.960 L/min |
| 15μ | 98.65% | 6.74% | 0.15% | 0.933 L/min |

The liquid recovery data was normalized to the highest yield examined over the data set, the moisture content if the solid cake was measured via vacuum oven digestion, and the suspended solids were determined via gyro-testing. Based on the data from Table 19, a 35 μfilter bag mesh was chosen for continued pilot study, and for full production. The liquid yield is maximized (over the sample set tested) utilizing the largest screen mesh. Unfortunately, this screen mesh also generates the highest amount of suspended solid in the filtered extract. It can be observed that a dramatic reduction in the amount of suspended solid is observed using filter bags below 75μ. The reduction of suspended solids achieved using a 35μfilter, combined with the acceptable yield and collection rate, made the 35μbag the preferred choice.

Although the invention has been described with respect to a preferred embodiment thereof, it is to be also understood that it is not to be so limited since changes and modifications can be made therein which are within the full intended scope of this invention as defined by the appended claims.

We claim:

1. A method for reducing post-prandial blood glucose levels in a human in need thereof, comprising the steps of:
   (a) preparing an alcohol-free extraction solution by adding to water an organic acid in a concentration between 0.5 weight percent and 2.5 weight percent and a salt in an amount to provide between 0.3 and 2.0 normality with regard to the salt;
   (b) adding the plant material to the extraction solution in a weight ratio of between about 1:1 and about 1:10 extraction solution to plant material;
   (c) comminuting the plant material in the extraction solution to reduce the mean particle size of the plant material to between 100 microns and 1500 microns;
   (d) heating the solution to a temperature sufficient to denature at least Kunitz inhibitor proteins but below a temperature to denature proteinase inhibitor II;
   (e) filtering the heated solution of part (d) to remove the denatured proteins thereby obtaining a nutritional composition; and
   (f) administering to said human, prior to a meal, an effective amount of the nutritional composition of part (e) wherein said nutritional composition comprises between 1.0 mg and 1000 mg of proteinase inhibitor II and is substantially free of Kunitz inhibitors.

2. The method as defined in claim 1, wherein the administration of said nutritional composition reduces the initial blood glucose spike created after said human consumes said meal as compared to a blood glucose spike created when said human is not administered said nutritional composition.

3. The method as defined in claim 2, wherein the nutritional composition reduces the initial blood glucose spike by between 5 percent and 30 percent.

4. The method as defined in claim 1, wherein said nutritional composition is administered orally to provide a dose of between 0.5 and 20 mg of potato proteinase inhibitor II.

5. A method of treating hyperglycemia in a human in need thereof, comprising the steps of:
   (a) preparing an alcohol-free extraction solution by adding to water an organic acid in a concentration between 0.5 weight percent and 2.5 weight percent and a salt in an amount to provide between 0.3 and 2.0 normality with regard to the salt;
   (b) adding the plant material to the extraction solution in a weight ratio of between about 1:1 and about 1:10 extraction solution to plant material; and (c) comminuting the plant material in the extraction solution to reduce the mean particle size of the plant material to between about 100 microns and about 1500 microns;
(d) heating the solution to a temperature sufficient to denature at least Kunitz inhibitor proteins but below a temperature to denature proteinase inhibitor II;
(e) filtering the heated solution of part (d) to remove the denatured proteins thereby obtaining a nutritional composition; and
(f) administering to said human, 30 to 90 minutes prior to a meal, an effective amount of the nutritional composition of part (e) wherein said nutritional composition comprises between 1.0 mg and 1000 mg of proteinase inhibitor II and is substantially free of Kunitz inhibitors.

* * * * *

UNITED STATES PATENT AND TRADEMARK OFFICE
CERTIFICATE OF CORRECTION

PATENT NO. : 8,377,877 B2
APPLICATION NO. : 10/426678
DATED : February 19, 2013
INVENTOR(S) : Rod Ausich et al.

It is certified that error appears in the above-identified patent and that said Letters Patent is hereby corrected as shown below:

On the title page, item [75] inventor's name; "Zoriada DeFeitas" should be changed to Zoraida DeFreitas.

Signed and Sealed this
Twenty-sixth Day of March, 2013

Teresa Stanek Rea
*Acting Director of the United States Patent and Trademark Office*